(12) United States Patent
Arai et al.

(10) Patent No.: US 10,061,935 B2
(45) Date of Patent: Aug. 28, 2018

(54) INFORMATION PROCESSING APPARATUS, INFORMATION PROCESSING METHOD, AND STORAGE MEDIUM

(71) Applicant: FUJI XEROX CO., LTD., Tokyo (JP)

(72) Inventors: Kimiyoshi Arai, Kanagawa (JP); Noriyuki Kurabayashi, Tokyo (JP)

(73) Assignee: FUJI XEROX CO., LTD., Tokyo (JP)

( * ) Notice: Subject to any disclaimer, the term of this patent is extended or adjusted under 35 U.S.C. 154(b) by 229 days.

(21) Appl. No.: 15/055,683

(22) Filed: Feb. 29, 2016

(65) Prior Publication Data
US 2017/0076112 A1 Mar. 16, 2017

(30) Foreign Application Priority Data
Sep. 16, 2015 (JP) .................. 2015-182889

(51) Int. Cl.
*H04L 29/06* (2006.01)
*G06F 21/62* (2013.01)
*G06F 19/00* (2018.01)
*G06Q 50/24* (2012.01)
*G06Q 10/10* (2012.01)
*G16H 10/60* (2018.01)

(52) U.S. Cl.
CPC .......... *G06F 21/6245* (2013.01); *G06F 19/32* (2013.01); *G06Q 10/10* (2013.01); *G06Q 50/24* (2013.01); *G16H 10/60* (2018.01); *G06F 2221/2137* (2013.01); *G06F 2221/2141* (2013.01)

(58) Field of Classification Search
CPC ...... G06F 21/31; G06F 21/60; G06F 21/6245; G06F 19/32; G06F 19/322; G06Q 50/24

USPC ...................... 726/27–30; 713/193
See application file for complete search history.

(56) References Cited

U.S. PATENT DOCUMENTS

| | | | | |
|---|---|---|---|---|
| 6,189,032 B1* | 2/2001 | Susaki | .................... | G06F 21/31 709/203 |
| 7,949,546 B1* | 5/2011 | Klieman | ............... | G06F 19/322 600/300 |
| 8,041,749 B2* | 10/2011 | Beck | ..................... | G06F 19/322 705/1.1 |
| 8,448,240 B2* | 5/2013 | Hammoutene | ..... | G06F 21/6245 705/22 |
| 9,390,228 B2* | 7/2016 | Reid | .................... | H04L 63/061 |

(Continued)

FOREIGN PATENT DOCUMENTS

| | | |
|---|---|---|
| JP | 2002-24386 A | 1/2002 |
| JP | 2014-16923 A | 1/2014 |

OTHER PUBLICATIONS

Information Communication System; Fukahori Kenichi, Sony Corp, Jan. 25, 2002(translation version of JP 2002024386).*

(Continued)

*Primary Examiner* — Hosuk Song
(74) *Attorney, Agent, or Firm* — Sughrue Mion, PLLC

(57) ABSTRACT

An information processing apparatus includes a memory that stores document data; a creating unit that creates access control information indicative of access control to the document data, the access control information being different depending on a group of a publication source of the document data; and a controller that controls an access to the document data by using the access control information.

13 Claims, 7 Drawing Sheets

(56) References Cited

U.S. PATENT DOCUMENTS

2006/0155583 A1     7/2006   Teshima et al.
2007/0240203 A1    10/2007   Beck

OTHER PUBLICATIONS

Communication dated Jan. 15, 2018 from the European Patent Office in counterpart application No. 16 160 152.1.
Flores, "Secure exchange of information in electronic health records", University of Wollongong Thesis Collection, Doctor of Philosophy thesis, School of Information Systems & Technology, University of Wollongong, Australia, Dec. 2010, http://ro.uow.edu.au/theses/3308. (230 pages total).

* cited by examiner

FIG. 5

<MEDICAL INSTITUTION MANAGEMENT TABLE>

| DEPARTMENT OF PUBLICATION SOURCE | MEDICAL INSTITUTION OF PUBLICATION DESTINATION CANDIDATE |
|---|---|
| CARDIOVASCULAR INTERNAL MEDICINE | X CLINIC |
| CARDIOVASCULAR INTERNAL MEDICINE | S MEDICAL OFFICE |
| CARDIOVASCULAR INTERNAL MEDICINE | Z HEART CLINIC |
| ELDERLY HYPERTENSIVE INTERNAL MEDICINE | V CLINIC |

FIG. 6

<ACCESS CONTROL INFORMATION, ACL>

| | HEART CT 38 | OPERATIVE RECORD 40 | DISCHARGE SUMMARY 42 | LABORATORY TEST REPORT 44 |
|---|---|---|---|---|
| CARDIOVASCULAR INTERNAL MEDICINE | · X CLINIC<br>· S MEDICAL OFFICE | · X CLINIC<br>· S MEDICAL OFFICE | · X CLINIC<br>· S MEDICAL OFFICE | |
| ELDERLY HYPERTENSIVE INTERNAL MEDICINE | | | V CLINIC | V CLINIC |

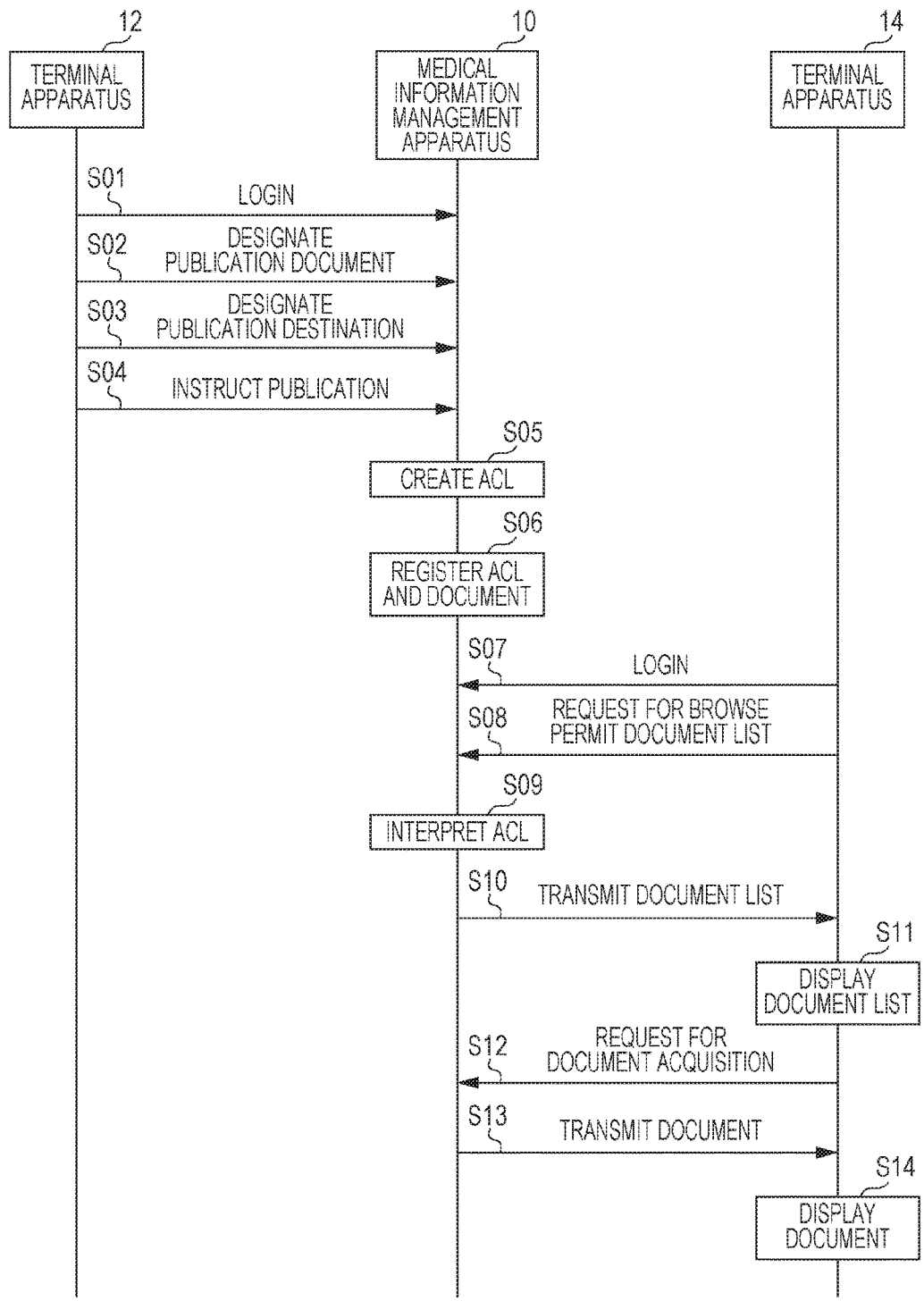

INFORMATION PROCESSING APPARATUS, INFORMATION PROCESSING METHOD, AND STORAGE MEDIUM

CROSS-REFERENCE TO RELATED APPLICATIONS

This application is based on and claims priority under 35 USC 119 from Japanese Patent Application No. 2015-182889 filed Sep. 16, 2015.

BACKGROUND (i) Technical Field

The present invention relates to an information processing apparatus, an information processing method, and a storage medium.

(ii) Related Art

An access to document data may be occasionally controlled.

SUMMARY

According to an aspect of the invention, there is provided an information processing apparatus including a memory that stores document data; a creating unit that creates access control information indicative of access control to the document data, the access control information being different depending on a group of a publication source of the document data; and a controller that controls an access to the document data by using the access control information.

BRIEF DESCRIPTION OF THE DRAWINGS

An exemplary embodiment of the present invention will be described in detail based on the following figures, wherein:

FIG. 5 illustrates an example of a medical institution management table;

FIG. 6 illustrates an example of access control information;

FIG. 8 is a sequence diagram showing processing in the medical information management system.

DETAILED DESCRIPTION

Figure 1:
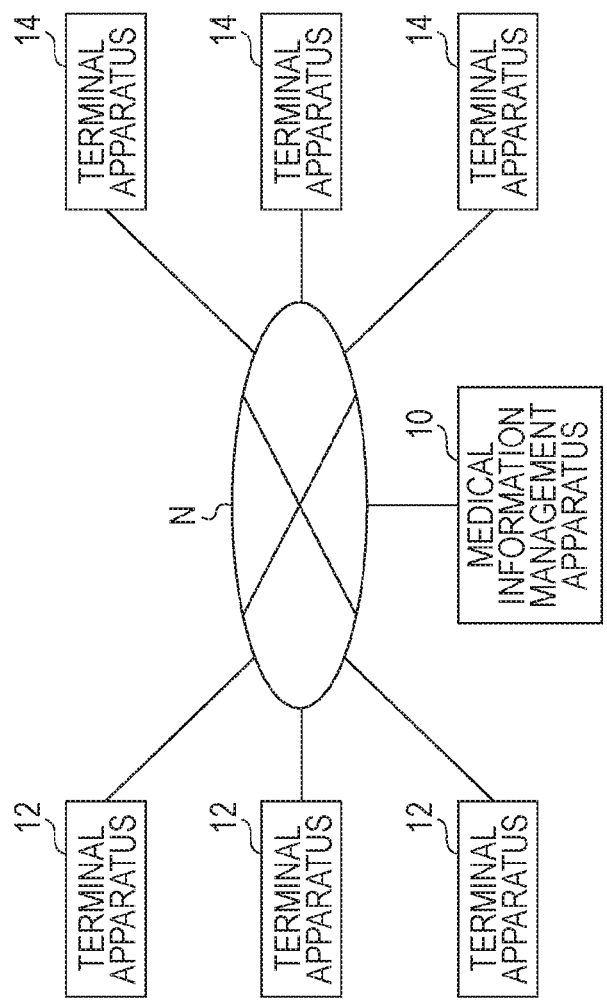
FIG. 1 is a block diagram showing a medical information management system according to an exemplary embodiment of the present invention.

FIG. 1 illustrates an example of a medical information management system serving as an information processing system according to an exemplary embodiment of the present invention. The medical information management system includes, for example, a medical information management apparatus 10 serving as an information processing apparatus, and terminal apparatuses 12 and 14. The medical information management apparatus 10 and the terminal apparatuses 12 and 14 are connected to a communication path N such as a network.

The medical information management apparatus 10 has a function of managing document data serving as medical information and providing the document data on demand. The medical information is, for example, an electronified medical chart (an electronic chart), information indicative of a letter of referral of a medical institution, a medical image (for example, X-ray CT image, a radiographic image, etc.), information indicative of a medical fee bill, and other information. For example, data of an electronic chart, data of a letter of referral, data of a medical image, data of a medical fee bill, and other data are managed as document data. Also, if a medical chart, a letter of referral, a medical fee bill, and other documents are created in sheets of paper, images on the sheets may be read by a scanner and document data (image data) generated accordingly may be managed.

The terminal apparatuses 12 and 14 each are, for example, any of apparatuses, such as a personal computer (PC), a tablet PC, a smart phone, and a cell phone, and each have a function of transmitting and receiving data to and from other apparatuses. The terminal apparatuses 12 and 14 each are arranged in, for example, any of medical institutions, such as a university hospital, a medical office, a clinic, and a private hospital. The terminal apparatus 12 is an apparatus to be used by a publication source of document data. The terminal apparatus 14 is an apparatus to be used by a publication destination of document data. In FIG. 1, three terminal apparatuses 12 and three terminal apparatuses 14 are connected to the communication path N; however, this is merely an example. A single terminal apparatus 12 and a single terminal apparatus 14 may be connected to the communication path N, or two or more terminal apparatuses 12 and two or more terminal apparatuses 14 may be connected to the communication path N.

In the medical information management system according to this exemplary embodiment, a user such as a doctor designates document data of a publication object and a publication destination of the document data by using the terminal apparatus 12. The medical information management apparatus 10 creates access control information for controlling an access to the document data in accordance with the designation. Also, if a user such as a doctor makes a request for an access to document data by using the terminal apparatus 14, the medical information management apparatus 10 controls the access to the document data by using access control information.

Figure 2:
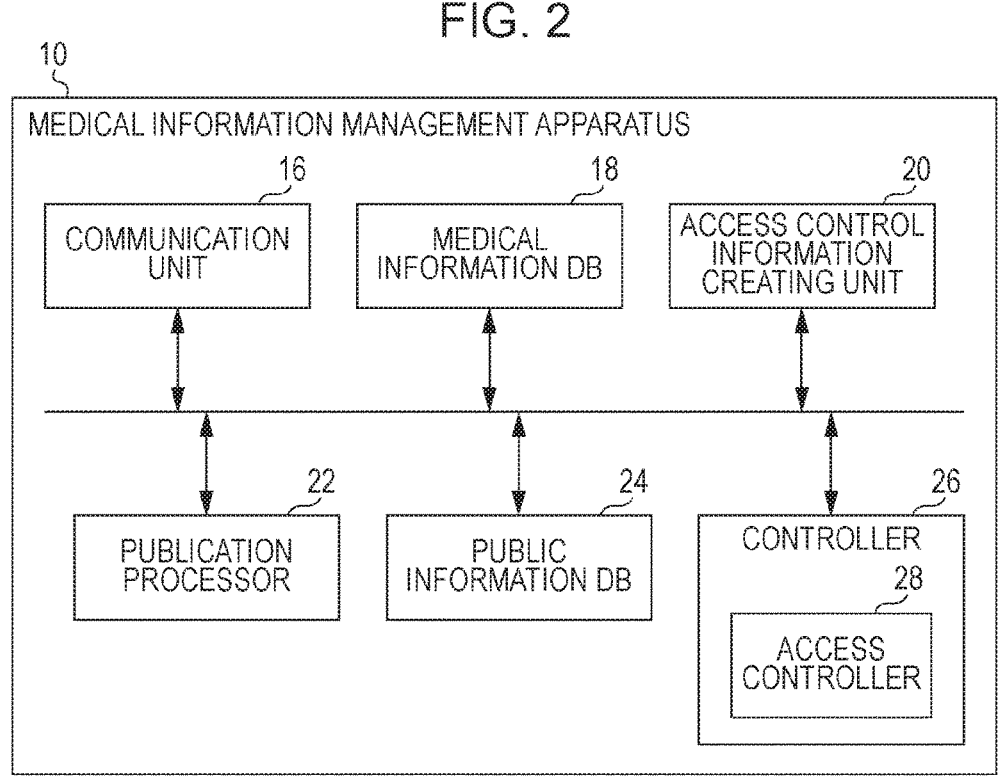
FIG. 2 is a block diagram showing a medical information management apparatus according to this exemplary embodiment.

A configuration of the medical information management apparatus 10 is described below in detail with reference to FIG. 2. FIG. 2 illustrates the configuration of the medical information management apparatus 10.

A communication unit 16 is a communication interface, and has a function of transmitting data to other apparatuses and a function of receiving data from other apparatuses.

A medical information database (medical information DB) 18 is a memory device such as a hard disk. The medical information DB 18 stores document data serving as medical information. The document data is associated with document management information for managing the document data. The document management information includes, for example, document identification information for identifying the document data (for example, a document ID), information indicative of the version of the document data (for example, a version number), document type information indicative of the type of a document (for example, a document type code), information indicative of the title of the document, and information indicative of the created date of the document data. Also, the document data is associated with patient information. The patient information includes, for example, patient identification information for identifying a patient (for example, a name or a patient ID), information indicative of the sex of the patient, information indicative of the birth date of the patient, and information indicative of the age of the patient. For example, every time when document data such as an electronic chart is created, the document data is stored in the medical information DB 18. The document data stored in the medical information DB is shared by a publication source. That is, the document data stored in the medical information DB is data permitted to be accessed from the terminal apparatus 12.

Also, the medical information DB 18 stores medical institution information relating to a medical institution registered in the medical information management system. The medical institution is a medical institution of a publication destination candidate of the document data. The medical institution information includes, for example, medical institution identification information for identifying the medical institution (for example, an institution name or an institution ID). Alternatively, the medical institution information may be stored in another memory device.

The medical information DB 18 may not be provided in the medical information management apparatus 10, and may be provided in another apparatus connected to the communication path N.

An access control information creating unit 20 has a function of creating access control information indicative of access control to the document data of the publication object, the access control information being different depending on a publication source group of the document data. The access control information creating unit 20 creates access control information, for example, every document data. A single piece of access control information may be created for a single piece of document data, and plural pieces of access control information may be created for a single piece of document data. For example, if access control is set for certain document data by a single publication source group, a single piece of access control information is created for the document data. In contrast, if access control is set for certain document data by plural publication source groups, plural pieces of access control information are created for the document data. In this case, access control information is created every publication source group, and consequently, the same number of pieces of access control information as the number of publication source groups are created.

The access control information includes, for example, publication source information relating to a publication source group, document management information about document data of a publication object, patient information associated with the document data, and publication destination information relating to a publication destination. The publication source group and the publication destination each may be, for example, a medical institution, a department in the medical institution, or an area of a prefecture or a municipality.

The publication destination information includes, for example, publication destination identification information for identifying a publication source group (for example, a publication source name or a publication source ID) and publication setting user identification information for identifying a publication setting user (for example, a publication source user name or a publication source user ID). If the unit of the publication source group is a medical institution, such as a hospital, a medical office, or a clinic, the publication source information includes, as the publication source identification information, medical institution identification information for identifying the medical institution (for example, a medical institution name or a medical institution ID). If the unit of the publication source group is a department, the publication source information includes, as the publication source identification information, medical institution identification information for identifying a medical institution to which the department belongs to (for example, a medical institution name or a medical institution ID) and department identification information for identifying the department (for example, a department name or a department ID). If the unit of the publication source group is an area, the publication source information includes, as the publication source identification information, area identification information for identifying the area (for example, an area name or an area ID). The publication source information may be transmitted from the terminal apparatus 12 that is used by the publication source group to the medical information management apparatus 10, for example, at publication processing, or may be previously stored in the medical information DB 18 of the medical information management apparatus 10.

The publication destination information includes, for example, publication destination identification information for identifying a publication destination (for example, a publication destination name or a publication destination ID). If the unit of the publication destination is a medical institution, such as a hospital, a medical office, or a clinic, the publication destination information includes, as the publication destination identification information, medical institution identification information for identifying the medical institution (for example, a medical institution name or a medical institution ID). If the unit of the publication destination group is a department, the publication destination information includes, as the publication destination identification information, medical institution identification information for identifying a medical institution to which the department belongs to (for example, a medical institution name or a medical institution ID) and department identification information for identifying the department (for example, a department name or a department ID). If the unit of the publication destination is an area, the publication destination information includes, as the publication destination identification information, area identification information for identifying the area (for example, an area name or an area ID). The publication destination information is previously transmitted from the publication destination to the medical information management apparatus 10, and is previously stored in the medical information DB 18 of the medical information management apparatus 10. For example, when a medical institution or a department of a publication destination is registered in the medical information management system, publication destination information is transmitted from the publication destination to the medical information management apparatus 10 and is stored.

For example, if a user such as a doctor designates document data of a publication object and a publication destination of the document data by using the terminal apparatus 12 in a publication source group, the access control information creating unit 20 creates access control information for controlling an access to the document data in accordance with the designation.

As described above, the access control information includes the patient information and the publication source information. The access control information creating unit 20 permits a change in the access control information by the group indicated by the publication source information included in the access control information, but inhibits a change in the access control information by a group other than the group indicated by the publication source information. For example, if the publication source information included in the access control information includes department identification information indicative of a department A, a change in the access control information by a doctor belonging to the department A is permitted, but a change in the access control information by a doctor belonging to a department other than the department A is inhibited. For example, if a user such as a doctor inputs patient information and publication source information by using the terminal apparatus 12 and hence makes a request for an access to access control information, the access control information creating unit 20 permits an access to access control information including the input patient information and publication source information, and permits a change in the access control information. In contrast, the access control information creating unit 20 inhibits an access to access control information not including the input patient information or publication source information, and inhibits a change in the access control information. In this way, the access control information is managed individually on a group basis.

A publication processor 22 has a function of registering document data of a publication object and access control information for the document data in an associated manner. The document data and the access control information are associated with each other and stored in a public information database (DB) 24.

The public information DB 24 is a memory device such as a hard disk. The public information DB 24 stores document data of a publication object and access control information for the document data in an associated manner.

A controller 26 has a function of controlling operations of respective units of the medical information management apparatus 10. Also, the controller 26 includes an access controller 28.

The access controller 28 has a function of controlling an access to document data by using access control information. For example, if a user such as a doctor makes a request for an access to document data by using the terminal apparatus 14, the access controller 28 controls the access to the document data by using access control information associated with the document data being an object of the access request. If the access request is an access request from a publication destination, the access to the document data is permitted. In contrast, if the access request is an access request not from a publication destination, the access to the document data is inhibited.

Figure 3:
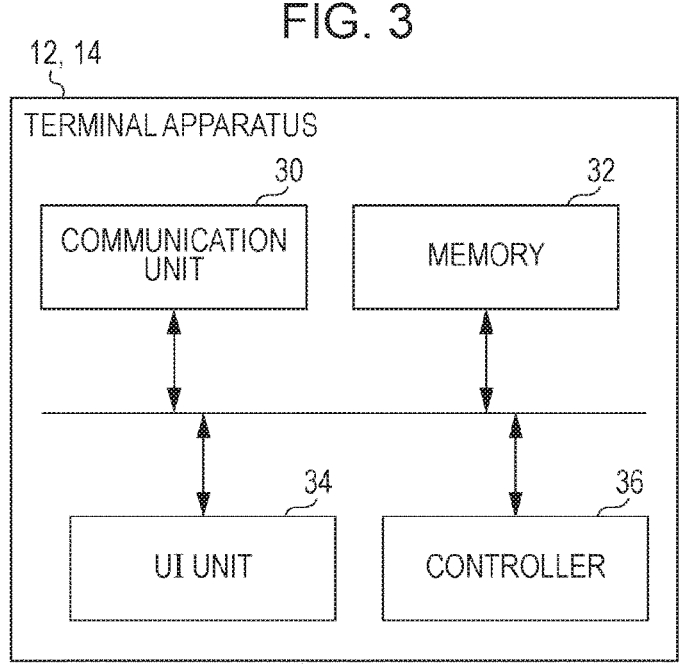
FIG. 3 is a block diagram showing a terminal apparatus.

A configuration of each of the terminal apparatuses 12 and 14 is described below in detail with reference to FIG. 3. FIG. 3 illustrates the configuration of the terminal apparatus 12. The terminal apparatus 14 has the same configuration as the terminal apparatus 12. A communication unit 30 is a communication interface, and has a function of transmitting data to other apparatuses and a function of receiving data from other apparatuses. A memory 32 is a memory device such as a hard disk. A UI unit 34 is a user interface, and includes a display and an operation unit. The display is a display device such as a liquid crystal display. The operation unit is an input device, such as a touch panel or a keyboard. A controller 36 controls operations of respective units of the terminal apparatus 12.

Figure 4:
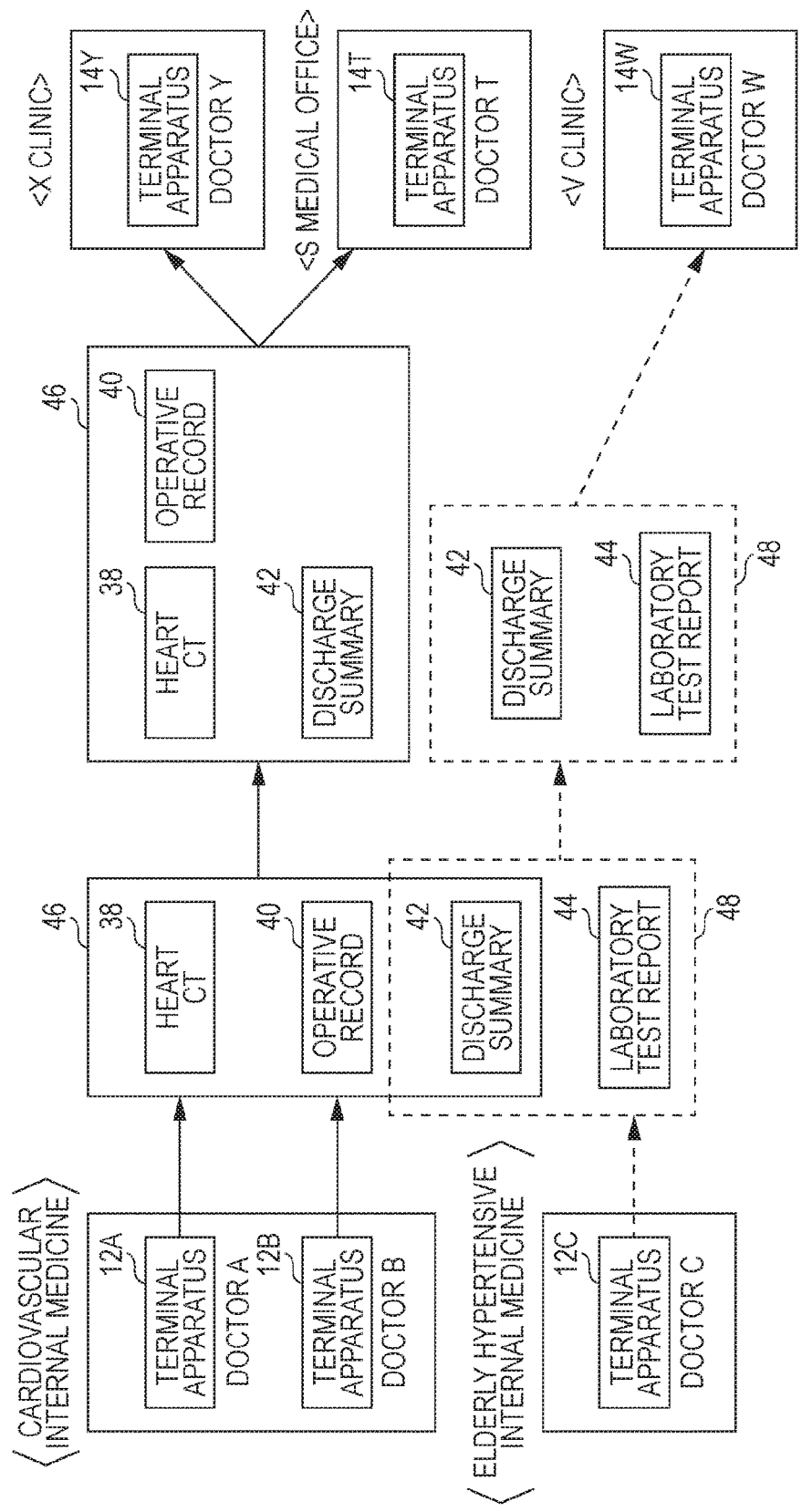
FIG. 4 is an illustration for describing an overview of processing in the medical information management system.

An overview of processing in the medical information management system is described below with reference to FIG. 4. FIG. 4 is an illustration for describing the overview of the processing.

Terminal apparatuses 12A, 12B, and 12C are examples of the terminal apparatus 12, and are terminal apparatuses that are used in, for example, a medical institution of a publication source (for example, a university hospital). Cardiovascular internal medicine and elderly hypertensive internal medicine are examples of departments in the university hospital, and correspond to examples of publication source groups. The terminal apparatuses 12A and 12B are terminal apparatuses that are used in the cardiovascular internal medicine in the university hospital, and the terminal apparatus 12C is a terminal apparatus that is used in the elderly hypertensive internal medicine in the same university hospital.

Terminal apparatuses 14Y, 14T, and 14W are examples of the terminal apparatus 14, and are terminal apparatuses that are used in medical institutions of publication destinations. To be more specific, the terminal apparatus 14Y is a terminal apparatus that is used in an X clinic as a medical institution, the terminal apparatus 14T is a terminal apparatus that is used in an S medical office as a medical institution, and the terminal apparatus 14W is a terminal apparatus that is used in a V clinic as a medical institution. Publication destination information (medical institution information) about the X clinic, S medical office, and V clinic are previously stored in the medical information DB 18 of the medical information management apparatus 10.

For example, it is assumed that diagnosis and treatment are executed on, for example, a patient P, and a heart CT image 38, operative record information 40, discharge summary information 42, and a laboratory test report 44 are created as document data (medical information). The heart CT image 38, the operative record information 40, the discharge summary information 42, and the laboratory test report 44 are associated with patient information on the patient P and stored in the medical information DB 18. The document data are data shared in, for example, the university hospital, and data permitted to be accessed from the terminal apparatuses 12A, 12B, and 12C.

The heart CT image 38, the operative record information 40, and the discharge summary information 42 are document data belonging to a publication document group 46. The discharge summary information 42 and the laboratory test report 44 are document data belonging to a publication document group 48.

The document data belonging to the publication document group 46 is data designated as publication document data by doctors A and B belonging to the cardiovascular internal medicine. The document data belonging to the publication document group 48 is data designated as publication document data by a doctor C belonging to the elderly hypertensive internal medicine. In the example shown in FIG. 4, the discharge summary information 42 belongs to both the publication document group 46 and the publication document group 48. That is, the discharge summary information 42 is designated as document data of a publication object by both the doctors of the cardiovascular internal medicine and the elderly hypertensive internal medicine.

By the doctors A and B belonging to the cardiovascular internal medicine, the X clinic and the S medical office are designated as medical institutions of publication destinations. Therefore, the document data belonging to the publication document group 46 is data permitted to be accessed from the X clinic (the terminal apparatus 14Y) and the S medical office (the terminal apparatus 14T).

Also, by the doctor C belonging to the elderly hypertensive internal medicine, the V clinic is designated as a medical institution of a publication destination. Therefore, the document data belonging to the publication document group 48 is data permitted to be accessed from the V clinic (the terminal apparatus 14W).

As described above, the department of the publication source, the document data of the publication object, and the medical institution of the publication destination are associated with each other, and the document data of the publication object and the medical institution of the publication destination are individually set every department of the publication source.

The medical information management apparatus 10 is described below in further detail.

Example of a medical institution registered in the medical information management system are described with reference to FIG. 5. FIG. 5 illustrates an example of a medical institution management table. The medical institution management table is an example of medical institution information. The data of the medical institution management table is previously created and stored in the medical information DB 18. A department of a publication source is an example of a publication source group of document data. As examples of the department of the publication source, cardiovascular internal medicine and elderly hypertensive internal medicine are registered. The cardiovascular internal medicine and the elderly hypertensive internal medicine are, for example, departments in the same university hospital. A medical institution of a publication destination candidate is a medical institution of a publication destination candidate of document data. As examples of the medical institution of the publication destination candidate, an X clinic, an S medical office, a Z heart clinic, and a V clinic are previously registered. In the example shown in FIG. 5, the cardiovascular internal medicine is associated with the X clinic, the S medical office, and the Z heart clinic, and the elderly hypertensive internal medicine is associated with the V clinic. That is, the X clinic, the S medical office, and the Z heart clinic are registered as medical institutions of publication destination candidates of document data to be publicized by a user such as a doctor belonging to the cardiovascular internal medicine, and the V clinic is registered as a medical institution of a publication destination candidate of document data to be publicized by a user such as a doctor belonging to the elderly hypertensive internal medicine. To select a medical institution of a publication destination, the user belonging to the cardiovascular internal medicine selects a medical institution of a publication destination from the X clinic, the S medical office, and the Z heart clinic. The user belonging to the elderly hypertensive internal medicine selects the V clinic as a medical institution of a publication destination.

Access control information is described below in detail with reference to FIG. 6. FIG. 6 illustrates an example of access control information (access control list, ACL). The access control information is created in response to an instruction of a user of a publication source, and stored in the public information DB 24. Access control information being different depending on a publication source group is created. If the unit of the publication source group is a department, access control information being different depending on a department is created. In the example shown in FIG. 6, the heart CT image 38, the operative record information 40, and the discharge summary information 42 are designated as document data of a publication object of a patient P, and the X clinic and the S medical office are designated as medical institutions of publication destinations by a user belonging to the cardiovascular internal medicine of a publication source. Accordingly, in access control information created in response to the instruction of the user belonging to the cardiovascular internal medicine, patient information on the patient P, publication source information on a cardiovascular internal medicine, document management information about the document data of the publication object (the heart CT image 38, the operative record information 40, and the discharge summary information 42), and publication destination information on medical institutions of the publication destinations (the X clinic and the S medical office) are associated with each other. Also, the discharge summary information 42 and the laboratory test report 44 are designated as document data of a publication object of the patient P by a user belonging to the elderly hypertensive internal medicine of a publication source, and the V clinic is designated as a medical institution of a publication destination. Accordingly, in the access control information created in response to the instruction of the user belonging to the elderly hypertensive internal medicine, patient information on the patient P, publication source information on the elderly hypertensive internal medicine, document management information about the document data of the publication object (the discharge summary information 42 and the laboratory test report 44), and publication destination information on the medical institution of the publication destination (the V clinic) are associated with each other. In this way, the different pieces of access control information are created for the cardiovascular internal medicine and the elderly hypertensive internal medicine. The access controller 28 controls an access from a medial institution of a publication destination to document data by referencing the access control information.

Figure 7:
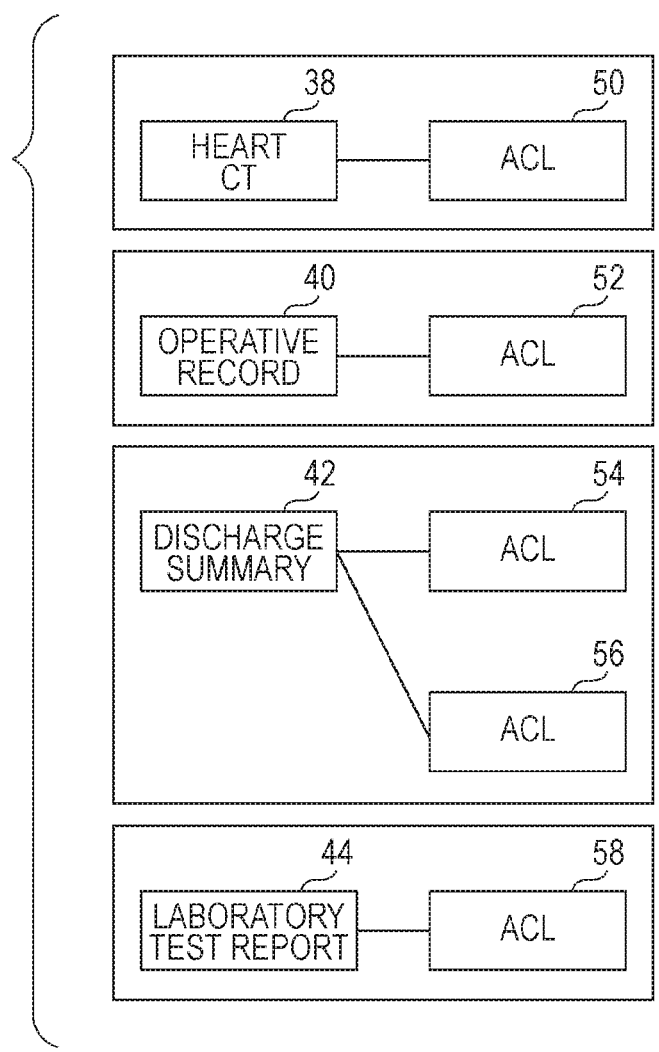
FIG. 7 illustrates correspondence between document data and access control information.

FIG. 7 illustrates an example of correspondence between document data and access control information (ACL). Access control information is created every document data of a publication object, and the document data and the access control information are associated with each other and stored in the public information DB 24.

For example, the heart CT image 38 and ACL 50 for controlling an access to the heart CT image 38 are associated with each other and stored in the public information DB 24. The ACL 50 includes patient information on a patient P, publication source information on the cardiovascular internal medicine of a publication source, document management information on the heart CT image 38, and publication destination information on medical institutions of publication destinations (the X clinic and the S medical office).

Similarly, the operative record information 40 and ACL 52 for controlling an access to the operative record information 40 are associated with each other and stored in the public information DB 24. The ACL 52 includes patient information on a patient P, publication source information on the cardiovascular internal medicine of a publication source, document management information on the operative record information 40, and publication destination information on medical institutions of publication destinations (the X clinic and the S medical office).

Similarly, the discharge summary information 42, and ACL 54 and ACL 56 for controlling an access to the discharge summary information 42 are associated with each other and stored in the public information DB 24. As described above with reference to FIGS. 4 and 6, the discharge summary information 42 is designated as the document data of the publication object by both the doctors of the cardiovascular internal medicine and the elderly hypertensive internal medicine. Therefore, the ACL 54 for the cardiovascular internal medicine and the ACL 56 for the elderly hypertensive internal medicine are created. The ACL 54 includes patient information on a patient P, publication source information on the cardiovascular internal medicine of a publication source, document management information on the discharge summary information 42, and publication destination information on medical institutions of publication destinations (the X clinic and the S medical office). Also, the ACL 56 includes patient information on a patient P, publication source information on the elderly hypertensive internal medicine of a publication source, document management information on the discharge summary information 42, and publication destination information on a medical institution of a publication destination (the V clinic).

Alternatively, the ACL 54 and ACL 56 may be included in single ACL. In this case, in the single ACL, an access from a user belonging to the cardiovascular internal medicine is permitted for a portion having written therein the ACL 54, and a change in the portion is permitted. In contrast, in the single ACL, an access from a user belonging to the elderly hypertensive internal medicine is permitted for a portion having written therein the ACL 56, and a change in the portion is permitted.

Similarly, the laboratory test report 44 and ACL 58 for controlling an access to the laboratory test report 44 are associated with each other and stored in the public information DB 24. The ACL 58 includes patient information on a patient P, publication source information on the elderly hypertensive internal medicine of a publication source, document management information on the laboratory test report 44, and publication destination information on a medical institution of a publication destination (the V clinic).

Processing in the medical information management system is described below in detail with reference to FIG. 8. FIG. 8 is a sequence diagram showing the processing.

First, a user of a publication source logs in the medical information management apparatus 10 by using the terminal apparatus 12 (S01). For example, it is assumed that the doctor A of the cardiovascular internal medicine logs in the medical information management apparatus 10 by using a user ID and a password for the cardiovascular internal medicine. Authentication at login is executed by, for example, the controller 26 of the medical information management apparatus 10. If a user ID and a password previously registered in the medical information management apparatus 10 match the user ID and the password input from the terminal apparatus 12, login is permitted. In case of mismatch, login is not permitted.

Then, the user of the publication source (the doctor A of the cardiovascular internal medicine) designates document data of a publication object by using the terminal apparatus 12 (S02). For example, a list of document data stored in the medical information DB 18 is displayed on the UI unit 34 of the terminal apparatus 12. Document data of a publication object is designated by the user (the doctor A of the cardiovascular internal medicine) from the list.

Also, the user of the publication source (the doctor A of the cardiovascular internal medicine) designates a publication destination by using the terminal apparatus 12 (S03). For example, a medical institution of a publication destination is designated from a medical institution group registered in the medical information management system. If the user of the publication source is the doctor A of the cardiovascular internal medicine, a medical institution of a publication destination is designated from a medical institution group of publication destination candidates corresponding to the cardiovascular internal medicine. In the example shown in FIG. 5, the X clinic, the S medical office, and the Z heart clinic are registered as medical institutions of publication destination candidates corresponding to the cardiovascular internal medicine. For example, a list of the medical institutions of the publication destination candidates is displayed on the UI unit 34 of the terminal apparatus 12. A medical institution of a publication destination is designated by the user (the doctor A of the cardiovascular internal medicine) from the list.

Then, the user of the publication source (the doctor A of the cardiovascular internal medicine) instructs publication of the document data by using the terminal apparatus 12 (S04).

In the medical information management apparatus 10, the access control information creating unit 20 creates access control information (ACL) (S05). For example, as shown in FIG. 6, it is assumed that the doctor A of the cardiovascular internal medicine designates the heart CT image 38, the operative record information 40, and the discharge summary information 42 as document data of a publication object, and designates the X clinic and the S medical office as medical institutions of publication destinations. In this case, the access control information creating unit 20 creates access control information for the heart CT image 38, access control information for the operative record information 40, and access control information for the discharge summary information 42. For example, as shown in FIG. 7, the ACL 50 is created for the heart CT image 38, the ACL 52 is created for the operative record information 40, and the ACL 54 is created for the discharge summary information 42.

The publication processor 22 associates the document data of the publication object with the access control information for the document data, and stores the document data and the access control information in the public information DB 24 (S06).

Even when document data is publicized by the doctor C of the elderly hypertensive internal medicine, processing similar to the above-described processing is executed. Accordingly, access control information for the elderly hypertensive internal medicine is created. For example, as shown in FIG. 6, it is assumed that the doctor C of the elderly hypertensive internal medicine designates the discharge summary information 42 and the laboratory test report 44 as document data of publication objects, and designates the V clinic as a medical institution of a publication destination. In this case, the access control information creating unit 20 creates access control information for the discharge summary information 42 and access control information for the laboratory test report 44. For example, as shown in FIG. 7, the ACL 56 is created for the discharge summary information 42, and the ACL 58 is created for the laboratory test report 44.

When a user of a publication destination makes an access to document data, the user of the publication destination logs in the medical information management apparatus 10 by using the terminal apparatus 14 (S07). For example, it is assumed that the doctor Y of the X clinic logs in the medical information management apparatus 10 by using a user ID and a password. Authentication at login is executed by, for example, the controller 26 of the medical information management apparatus 10. If a user ID and a password previously registered in the medical information management apparatus 10 match the user ID and the password input from the terminal apparatus 14, login is permitted. In case of mismatch, login is not permitted.

Then, the user of the publication destination (the doctor Y of the X clinic) makes a request for a list of document data permitted to be browsed by the user, by using the terminal apparatus 14 (S08). At this time, publication destination information is transmitted from the terminal apparatus 14 to the medical information management apparatus 10. The publication destination information includes medical institution identification information for identifying the X clinic (for example, the name or ID of the X clinic).

In the medical information management apparatus 10, the access controller 28 interprets access control information (ACL) stored in the public information DB 24 (S09). Accordingly, the access controller 28 specifies document data permitted to be browsed by the user of the publication destination (the doctor Y of the X clinic). To be specific, the access controller 28 references access control information including medical institution identification information transmitted from the terminal apparatus 14 as publication destination information, and specifies document data associated with the medical institution identification information, as document data permitted to be browsed by the user of the publication destination. Then, the access controller 28 transmits data of a list of document data permitted to be browsed by the user of the publication destination, to the terminal apparatus 14 (S10). The list of the document data permitted to be browsed is displayed on the UI unit 34 of the terminal apparatus 14 (S11).

For example, as shown in FIG. 6, the heart CT image 38, the operative record information 40, and the discharge summary information 42 are publicized to the X clinic. Accordingly, an access to the heart CT image 38, the operative record information 40, and the discharge summary information 42 is permitted. In this case, the access controller 28 transmits the data of the list of the document data permitted to be publicized to the X clinic, to the terminal apparatus 14. Accordingly, the list of the heart CT image 38, the operative record information 40, and the discharge summary information 42 is displayed on the UI unit 34 of the terminal apparatus 14 of the X clinic.

Then, the user of the publication destination (the doctor Y of the X clinic) designates document data being an acquisition object from the list of the document data displayed on the UI unit 34 and makes a request for acquisition of the document data by using the terminal apparatus 14 (S12). Accordingly, information for identifying the document data designated by the user is transmitted from the terminal apparatus 14 to the medical information management apparatus 10.

In the medical information management apparatus 10, the access controller 28 acquires the document data being the acquisition object, which is designated by the user, from the public information DB 24, and transmits the document data to the terminal apparatus 14 (S13). In the terminal apparatus 14, the document data is displayed on the UI unit 34 (S14).

For example, when the heart CT image 38 is designated by the doctor Y of the X clinic, data (document data) of the heart CT image 38 is transmitted from the medical information management apparatus 10 to the terminal apparatus 14, and the heart CT image 38 is displayed on the UI unit 34 of the terminal apparatus 14.

Even when the doctor T of the S medical office or the doctor W of the V clinic is a user of a publication destination, processing similar to the above-described processing is executed. For example, when a request is made for acquisition of document data by the doctor T of the S medical office, a list of the heart CT image 38, the operative record information 40, and the discharge summary information 42 is displayed on the UI unit 34 of the terminal apparatus 14, as a list of document data permitted to be browsed. When a request is made for acquisition of document data by the doctor W of the V clinic, a list of the discharge summary information 42 and the laboratory test report 44 is displayed on the UI unit 34 of the terminal apparatus 14, as a list of document data permitted to be browsed.

As described above, in this exemplary embodiment, different access control information is generated on a publication source group basis, and an access to document data is controlled based on the access control information. The access control information is individually managed on a group basis, and an access to access control information set by one group from the other group is inhibited. Accordingly, the access control information set by the one group is not changed by the other group. Therefore, on the basis of a publication source group of document data, access control to the document data is provided.

For example, access control information set by a doctor belonging to the doctor's department is not changed by a doctor belonging to another department. Accordingly, on the basis of a department of a publication source of document data, access control to the document data is provided. For example, when respective departments are independent in the same hospital, even if the same medical information management system is used, independence of each department is ensured for access control to document data.

In the above-described example, a department is a publication source group, and access control information is created every individual department. However, even when the publication source group is a medical institution or an area, independence of each group is ensured for access control to document data similarly to the case of the department. For example, if plural medical institutions are registered in the medical information management system as publication source groups, access control information is created every medical institution, and access control information set by one medical institution is not changed by the other medical institution. Accordingly, even when the same medical information management system is used, independence of each medical institution is ensured for access control to document data.

If the publication source group is a medical institution or an area, it may be expected that the medical information management system according to this exemplary embodiment is applied to local medical care. In this case, by using the medical information management system according to this exemplary embodiment, access control to medical information in the local medical care is provided.

With this exemplary embodiment, by updating access control information without updating document data itself, access control to document data is changed. For example, when plural publication source groups set access control to the same document data in accordance with the convenience of each group, only access control information may be created or updated in accordance with the convenience of each group without updating the document data itself.

A modification is described below. When publication processing is applied to document data stored in the medical information DB 18, a template named default publication document type may be used. The default publication document type is a type of document data of a publication object, and the template indicates the type. For example, when a user belonging to a publication source group logs in the medical information management apparatus 10 and instructs application of publication processing, the access control information creating unit 20 specifies the type of document data of a publication object by referencing the template and treats the document data corresponding to the default publication document type as document data of a publication object. Document management information on document data includes a document type code indicative of a document type. By referencing the document type code, the type of the document data is specified. Access control information about the publication source group includes document management information on the document data corresponding to the default publication document type and publication destination information about a publication destination designated by a user belonging to the publication source group. Accordingly, an access from the publication destination to the document data corresponding to the default publication document type is permitted. For example, if the default publication document type is an electronic chart, the electronic chart is treated as a publication object. By using the default publication document type, as compared with a case without the use of the default publication document type, work of the user relating to the publication processing is simplified. Further, for example, if "document classified into inspection record" is set in the default publication document type, a document of an inspection record of, for example, a blood test, a stomach endoscopic examination, or a chest X-ray examination is treated as a publication object.

As another modification, when the publication processing is applied to document data which will be registered in the medical information DB 18 in future, a template named automatic publication document type may be used. The automatic publication document type is a type of document data of a publication object, and the template indicates the type. When document data is newly stored in the medical information DB 18, the access control information creating unit 20 specifies the type of the document data of the publication object by referencing the template. If the type of the newly registered document data corresponds to the pubic document type, the access control information creating unit 20 treats the document data as a publication object. In this case, access control information includes document management information on the document data. By using the automatic publication document type, as compared with a case without the use of the automatic publication document type, work of a user relating to the publication processing is simplified.

Also, a publication period of document data may be set. The publication period is a period in which an access to document data from a publication destination is permitted. The access controller 28 permits an access to the document data from the publication destination in the publication period, and inhibits an access to the document data from the publication destination outside the publication period. Information indicative of the publication period is included in access control information. The access controller 28 controls an access depending on the publication period by referencing the information. Accordingly, an access to the document data is automatically inhibited when the publication period has elapsed. The user of the publication source does not have to stop the publication.

In this exemplary embodiment, when at least one of a publication source group, document data of a publication object, and a state of a publication destination is changed, access control information relating to the change is updated, or new access control information is created. For example, if at least one of states including a publication flag of document data, a publication period, a publication destination (medical institution, medical office, area, etc.), a publication destination permitted for publication by a publication source group, a publication destination facility master, an automatic publication document type, an automatic publication period, a default publication document type of the publication source group, a document type permitted for publication by the publication source group, a defined document type, a department, a patient or a user, document data, a version of the document data, a publication tag of the document data, a document type, is changed, access control information relating to the change in the state is updated or new access control information is created. The other access control information not relating to the above-described change in the state is not influenced, or updated by the change in the state. That is, individual control information is independent from the other access control information. Even when a state relating to certain access control information is changed, the other access control information is not influenced, or updated by the change in the state.

When publication of document data is stopped, document data of a publication stop object may be deleted from the public information DB 24, and access control information associated with the document data may be left in the public information DB 24. Accordingly, leakage of the document data of the publication stop object may be prevented, and information relating to access control may be provided to the publication destination.

The medical information management apparatus 10 is realized by, for example, cooperation of a hardware resource and software. To be specific, the medical information management apparatus 10 includes a processor such as a central processing unit (CPU) (not illustrated). The processor reads out a program stored in a memory device (not shown) and executes the program. Hence, the functions of the respective units of the medical information management apparatus 10 are realized. The program is stored in the memory device through a storage medium, such as a compact disc (CD) or a digital versatile disc (DVD), or a communication path such as a network. Alternatively, the respective units of the medical information management apparatus 10 may be realized by, for example, a hardware resource, such as a processor or an electronic circuit. A device such as a memory may be used for the realization. For another example, the respective units of the medical information management apparatus 10 may be realized by, for example, a digital signal processor (DSP) or a field programmable gate array (FPGA).

The foregoing description of the exemplary embodiment of the present invention has been provided for the purposes of illustration and description. It is not intended to be exhaustive or to limit the invention to the precise forms disclosed. Obviously, many modifications and variations will be apparent to practitioners skilled in the art. The embodiment was chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An information processing apparatus comprising:
a memory that stores document data; and
at least one hardware processor configured to implement:
a creating unit that creates access control information indicative of access control to the document data, the access control information being different depending on a group of a publication source of the document data; and
a controller that controls an access to the document data by using the access control information, wherein the group comprises a plurality of users of the publication source, and
wherein the group is separate from a second group comprising at least one user of the publication source other than the plurality of users.

2. The information processing apparatus according to claim 1,
wherein the document data is data relating to medical care, and
wherein the group is a medical institution or a department in the medical institution.

3. The information processing apparatus according to claim 1, wherein the creating unit creates the access control information to permit the access to the document data corresponding to a specific document type.

4. The information processing apparatus according to claim 1,
wherein the access control information includes information indicative of a period in which the access to the document data is permitted, and
wherein the controller permits the access to the document data in the period, and inhibits the access to the document data outside the period.

5. The information processing apparatus according to claim 1, wherein the access control information includes information indicative of a publication destination of the document data, and the access control information is updated by a change in at least one of the group of the publication source, the document data of an access object, and the publication destination.

6. The information processing apparatus according to claim 1,
wherein the group of the publication source includes a plurality of groups, and
wherein the creating unit creates the access control information different depending on an individual group included in the plurality of groups.

7. The information processing apparatus according to claim 6, wherein the document data is data that is shared by the plurality of groups.

8. A non-transitory computer readable medium storing a program causing a computer including a memory that stores document data to function as a configuration, the configuration comprising:
a creating unit that creates access control information indicative of access control to the document data, the access control information being different depending on a group of a publication source of the document data; and
a controller that controls an access to the document data by using the access control information,
wherein the group comprises a plurality of users of the publication source, and
wherein the group is separate from a second group comprising at least one user of the publication source other than the plurality of users.

9. An information processing method comprising:
storing document data;
creating access control information indicative of access control to the document data, the access control information being different depending on a group of a publication source of the document data; and
controlling an access to the document data by using the access control information,
wherein the group comprises a plurality of users of the publication source, and
wherein the group is separate from a second group comprising at least one user of the publication source other than the plurality of users.

10. The information processing apparatus according to claim 1,
wherein the creating unit creates the access control information of the document data in response to a request from at least one of the plurality of users of the group, and
wherein the creating unit further creates a second access control information of the document data in response to a second request from the second group.

11. The information processing apparatus according to claim 10,
wherein the request from the at least one of the plurality of users of the group indicates at least a first destination at which the document data may be accessed,
wherein the second request from the second group indicates at least a second destination at which the document data may be accessed, and
wherein the second destination is different than the first destination.

12. The information processing apparatus according to claim 11,
wherein the at least one hardware processor is further configured to implement:
providing a first listing of a first plurality of document data, including the document data, to the first destination according to the access control information and in response to a request from the first destination for the first listing,
providing a second listing of a second plurality of document data, including the document data, to the second destination according to the second access control information in response to a request from the second destination for the second listing, and
providing the document data to one of the first destination and the second destination in response to a selection of the document data from one of the first listing and the second listing provided to the one of the first destination and the second destination.

13. The information processing apparatus according to claim 1,
wherein the access control information indicates that at least one of the plurality of users of the group of the publication source selected a plurality of different groups, other than the group and the second group, which may access the document data,
wherein the plurality of different groups comprise a plurality of separate medical institutions, and
wherein the group and the second group comprise ones of separate departments in a same medical institution, different than the plurality of separate medical institutions.

* * * * *